(12) United States Patent
Neuberger et al.

(10) Patent No.: US 6,406,474 B1
(45) Date of Patent: Jun. 18, 2002

(54) DEVICE AND METHOD FOR APPLICATION OF RADIATION

(76) Inventors: Wolfgang Neuberger, Post Box 80599, 14 Hilltop Phase II, 87000 F.T. Labuan (MY); Michael Quade, Am Paulshuf 30, 53127 Bonn (DE)

( * ) Notice: Subject to any disclaimer, the term of this patent is extended or adjusted under 35 U.S.C. 154(b) by 0 days.

(21) Appl. No.: 09/409,358

(22) Filed: Sep. 30, 1999

(51) Int. Cl.⁷ .............................................. A61B 18/18
(52) U.S. Cl. ................................................ 606/9; 606/3
(58) Field of Search .......................... 606/9, 16, 10–12; 607/6, 7; 250/234, 227.26; 128/898

(56) References Cited

U.S. PATENT DOCUMENTS

| | | | | |
|---|---|---|---|---|
| 4,733,660 A | * | 3/1988 | Itzkan ..................... | 128/303.1 |
| 5,286,970 A | * | 2/1994 | Betzig et al. .......... | 250/227.26 |
| 5,288,996 A | * | 2/1994 | Betzig et al. .......... | 250/227.26 |
| 5,410,151 A | * | 4/1995 | Buckland ............... | 250/227.26 |
| 5,485,536 A | * | 1/1996 | Islam ........................ | 385/31 |
| 5,770,856 A | * | 6/1998 | Fillard et al. .............. | 250/234 |
| 5,860,967 A | * | 1/1999 | Zavislan et al. ............. | 606/9 |
| 5,971,978 A | * | 10/1999 | Mukai ......................... | 606/18 |

* cited by examiner

Primary Examiner—Peter J. Vrettakos

(57) ABSTRACT

A photonic scanning and delivery system capable of controllable transmission of light energy to an irregularly shaped treatment area are disclosed. The desired uniformity (controllability) of light energy application is ensured by a tracking device, which monitors the position of the radiation applicator and thereby prevents over- or under-radiation. The system employs a light energy delivery hand-piece. By these means, structures in the lower dermis are irradiated. Because of the large size of the treatment area, damage to surface tissue is avoided. The hand-piece can operate while in contact with the treatment surface. Treatment surfaces include non-medical work sites. Alternatively, the hand-piece can operate in a non-contact mode. The system can also be used in non-medical applications such as UV curing.

9 Claims, 6 Drawing Sheets

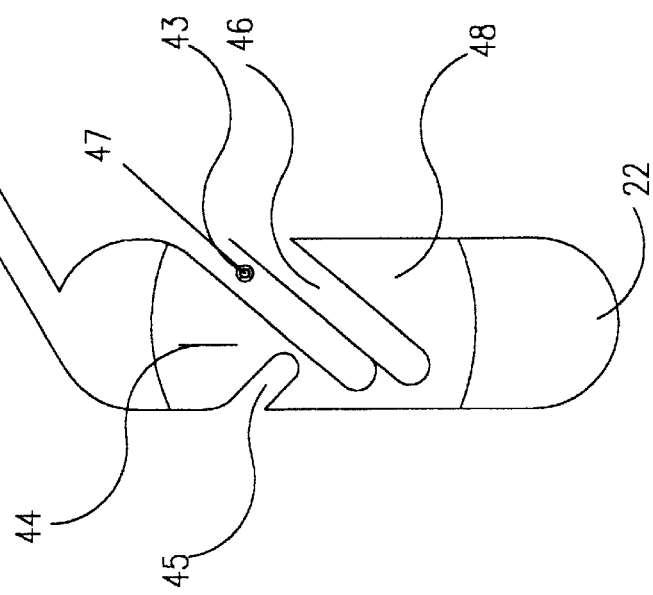
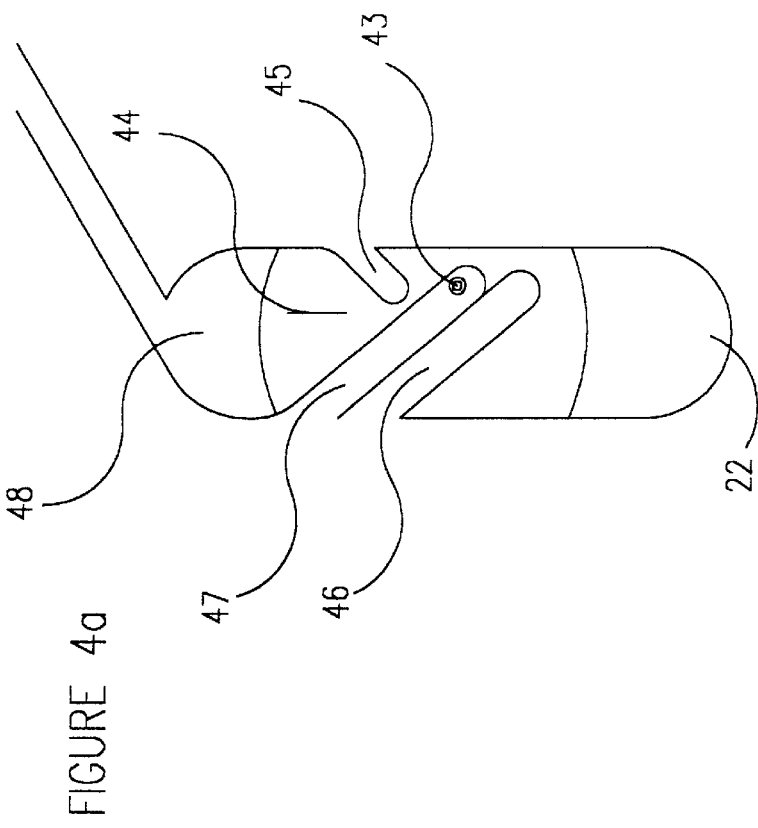
FIGURE 4b
FIGURE 4a

DEVICE AND METHOD FOR APPLICATION OF RADIATION

BACKGROUND OF THE INVENTION

1. Field of the Invention

The present invention relates to devices that deliver uniform quantities of light energy to treatment surfaces.

2. Information Disclosure Statement

Light energy is used in a multitude and variety of industrial and medical applications. For example, light energy may be employed for many cosmetic skin treatments including: 1) the removal of vascular lesions, benign pigmented lesions, and tattoos, 2) the abatement of blemishes within the lower dermis, 3) the removal of unwanted hair, 4) the creation of skin pockets during hair transplantation surgery, and 5) the shrinkage of varicose veins. These applications typically require light sources such as a pulsed dye, carbon dioxide, erbium, ruby, argon, alexandrite, copper vapor or Nd:YAG lasers. Additionally, diode light sources such as laser diodes, frequency-doubled laser diodes, tapered laser diodes, diode pumped solid state lasers, frequency-doubled diode pumped solid state lasers, diode pumped fiber lasers, or super luminescent diodes may be employed.

Most currently performed light energy (photonic) dermatology treatments involve either selective photothermolysis of pigmented structures within skin or involve char-free vaporization of skin. Selective photothermolysis is the precisely controlled destruction of unwanted pigmented structures in the skin. This process avoids significant harm to overlying or surrounding tissue that might result in scarring. Pigmented structures targeted by this method typically include melanin particles, enlarged blood vessels and tattoo ink particles. An operator selectively heats targeted structures until they are photo-coagulated or photo-disrupted, and the skin's natural physiological mechanisms break down and remove the light-altered remnants.

Selective photothermolysis removes tattoos by targeting the embedded ink particles. A wavelength that is well absorbed by the ink particle breaks up the particle, and the remnants then slough off. The procedure may require multiple wavelengths, depending on the number and kinds of inks used in the tattoo.

Hair removal is one of the largest potential markets for aesthetic photonic equipment and treatments. Hair removal methods rely on selective photothermolysis interactions with hair follicles. Although the underlying mechanisms are not completely understood, they most likely depend upon the type of light source and specific method employed. In one method, a carbon-based ointment is rubbed into the hair follicles. The carbon particles serve as the primary absorbers of light energy. In other "ointment free" methods, melanin particles lining the hair follicles are thought to absorb the light energy. The broad absorption curve of melanin—the natural skin pigment responsible for skin's brown color—allows selective heating of subsurface melanin particles by numerous visible and near-infrared wavelengths. Depending on the patient's skin color (melanin content), however, some wavelengths may be more effective because they better penetrate overlying skin.

Another important example of a target tissue present throughout the body is the vasculature that contains erythrocytes. The erythrocytes contain hemoglobin, a naturally occurring chromophore with a broad usable absorption band in the visible region. The entire range of visible wavelengths shorter than approximately 600 nm and extending into the ultraviolet is available to purposely inflict damage to target tissues containing this chromophore. The specific wavelength selected depends on 1) the relative effects of scattering, which varies with wavelength, 2) the presence of other chromophores, such as melanin, in the adjacent or overlying tissues, and 3) the availability of light sources.

The second major method of photonic dermatology treatment is char-free vaporization. In this method, certain types of light sources are employed to vaporize soft tissue with little or no carbonization, while also controlling bleeding. These qualities afford practitioners a high level of surgical precision and control. Removal of upper skin layers in areas with wrinkles, acne scars or other blemishes usually results in "de-emphasized" wrinkles or blemishes after healing. During the healing process, the patient can use makeup to hide reddened skin (erythema), which can last for weeks or months after the treatment.

"Non-ablative" methods represent a fundamentally new way to resurface the skin. Instead of vaporizing upper skin layers, light energy selectively heats collagen fibrils in subsurface layers, which stimulates the skin to make new collagen and "remodel" itself, de-emphasizing wrinkles. Selective heating of appropriate layers, several hundred microns below the surface may require simultaneous deposition of a coolant to the tissue surface to prevent damage to the epidermis (Manni, Jeffrey G., *Biophotonics International.* Vol. 5 (3), 1998, 40–7).

A method of applying coolant liquid to the skin surface to prevent tissue damage was also described in U.S. Pat. No. 5,454,807, entitled "Medical Treatment of Deeply Seated Tissue Using Optical Radiation", invented by Charles D. Lennox and Stephen P. Beaudet. The '807 patent is hereby expressly incorporated by reference as part of the present disclosure.

Simultaneous application of light energy and coolant in dermatological applications allows greater amounts of energy to be transferred to the dermis without injuring the overlying skin layers. Coolant applied at the treatment surface limits the elevated temperature range to the microvessels in the dermis to avoid any tissue damage and scar formation as a result of a dermatological procedure. The tissue surface can be cooled with a stream of fluid such as water, saline, and gaseous nitrogen, oxygen, or carbon dioxide.

In addition to simultaneous application of light energy and fluid material, it often is advantageous to uniformly distribute light energy to a larger surface area, e.g. a surface area of 10 $mm^2$ or larger. Uneven distribution of light energy may lead to too much or too little energy at certain portions of the work or treatment site. This can require re-treatment that is costly, and subjects the patient or the work piece to an increased risk of scarring (damage) or other problems that may occur during the procedure. For example, epidermis receiving too much light energy may become charred and change colors, leading to absorption of light energy destined for the dermis. Contrarily, if not enough light energy is applied to a site, the desired tissue change may not be attained. These negative effects are often realized in manual treatments because it is difficult to manually distribute energy uniformly. Thus, the skill of the practitioner in manual treatments has previously been of utmost importance for manually administered techniques.

In order to overcome the problems of non-uniformity of radiation, various scanning photonic delivery systems, typically incorporating a computerized sub-system, have been suggested. For example, Ortiz et al. (U.S. Pat. No. 5,474, 549) teach a system that provides for a uniform fluence level throughout a treatment site by scanning the light beam at a predetermined, controlled velocity (i.e. a controlled speed and direction), and predetermined pattern. However, the problem with this and other similar state of the art systems is that it is difficult to treat irregularly shaped areas that may be treatable by a manually operated photonic delivery system. State of the art computerized systems have a limited number of scan patterns, for example square, line, rectangle, rhombus, serpentine, triangle, or hexagon. Manually controlled scanners, however, can be manipulated to an unlimited number of scan patterns. An ideal laser scanning and delivery device, therefore, would offer the measured distribution of radiation of a computerized system and the scanning flexibility of manually controlled systems.

Additionally, computerized scanning systems can be very complicated, requiring intricate and expensive machinery. These systems may work well for a small two-dimensional treatment site, but may fail to treat larger three-dimensional formed areas or surfaces that are more commonly encountered in work and treatment applications. These three-dimensional treatment areas are commonly treated manually—a procedure inherently dependent on the skill of the operator.

U.S. Pat. No. 4,733,660 describes a light energy delivery hand-piece that provides an adjustable scanning mechanism that manipulates the dwell time of a focused light energy spot, thereby controlling the light energy absorbed by a target material. Specifically, the dwell time of the light energy beam is designed to match the thermal diffusion time for destruction of the wall of an abnormal vessel, and some surrounding collagen.

The Itzkan system of '660 fails to provide for a uniform distribution of energy throughout a work or treatment site. Moreover, it is difficult to determine the thermal diffusion time for destruction of the wall of an abnormal vessel because it depends on relative effects of light energy scattering, which varies in the presence of chromophores, such as melanin or erythrocytes in adjacent or overlying tissues. In exactly the conditions experienced in general application, the greatest problem with the Itzkan system is present.

It is therefore the aim of the present invention to provide a manually operated photonic scanning and delivery device that can deliver controlled amounts of energy to sites, especially irregularly shaped treatment or work sites.

OBJECTS AND SUMMARY OF THE INVENTION

It is therefore an object of the present invention to provide a manually operated photonic delivery system that can controllably deliver light energy to a treatment or work site.

It is another object of the present invention to provide a manually operated photonic delivery system that can uniformly deliver light energy to a treatment or work site.

It is yet another object of the present invention to provide a photonic delivery system that may be manually maneuvered in unlimited patterns to be especially applicable for if regularly shaped work or treatment sites.

It is an aim of the present invention is to provide a photonic system that may be operated in contact or non-contact mode.

Briefly stated, the present invention provides a photonic scanning and delivery system capable of controlled transmission of light energy to an irregularly shaped treatment area. The desired uniformity (controllability) of light energy application is ensured by a tracking device, which monitors the position of the radiation applicator and thereby prevents over-/under-radiation. The system employs a light energy delivery hand-piece. By these means, structures in the lower dermis are irradiated. The hand-piece can operate while in contact with a treatment surface. A treatment surface includes non-medical work sites. Alternatively, the hand-piece can operate in a non-contact mode. The system can also be used in non-medical applications such as UV or laser curing.

The above, and other objects, features and advantages of the present invention will become apparent from the following detailed description read in conjunction with the accompanying drawings. Items illustrated in different figures that have equivalent numbers are substantially identical.

BRIEF DESCRIPTION OF THE DRAWINGS

FIG. 4a portrays the outer shell of the hand-piece of the present invention.

FIG. 4b illustrates the left-handed version of the outer shell shown in FIG. 4a.

DETAILED DESCRIPTION OF PREFERRED EMBODIMENTS

Figure 1:
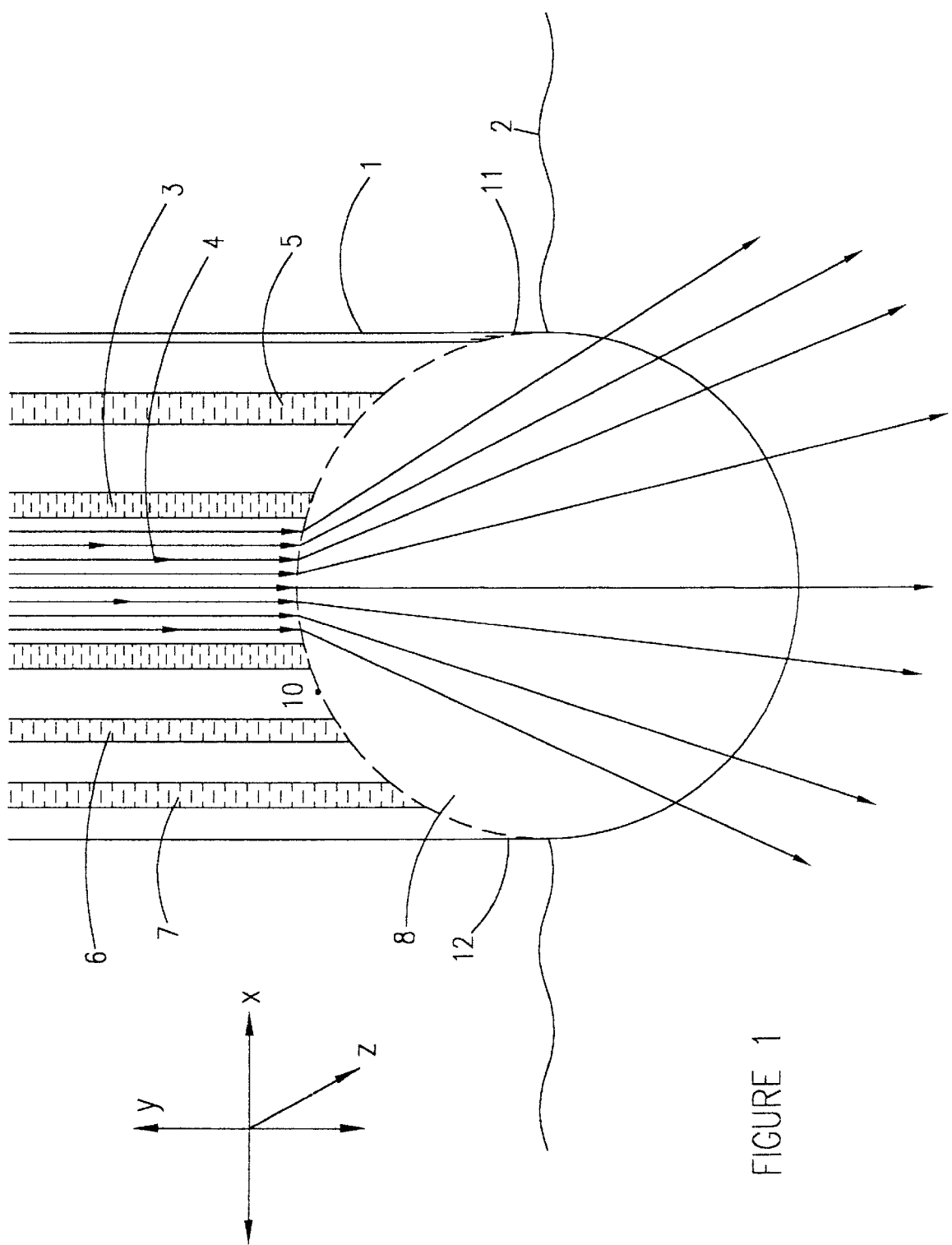
FIG. 1 illustrates a preferred embodiment of the present invention shown in side cut cross sectional view.

The present invention provides a device for delivery of light energy to a work or treatment site. An embodiment of the present invention shown in side cut cross sectional view is illustrated in FIG. 1. Light energy delivery hand-piece, represented generally by 9, is employed to deliver light energy to soft tissue treatment site 2. Application end 8 (tip) of light energy delivery hand-piece 9 can be solid or hollow and is preferably cylindrically shaped like a paint roller having approximately a 1 cm diameter and 2 cm width, although it may be spherically shaped having approximately a 2 cm diameter.

The most critical property of the material used for application end 8 is the transmission of pre-selected wavelengths with little or no scattering or absorption. For employment in applications with soft material sites, application end 8 ought to be a hard material, for example, a perfluoronated plastic, made from a Teflon®-like fluoropolymer. Alternatively, for use in applications with hard material sites, for example teeth, application end 8 should be a softer, more compliant material. Polymers or elastomers with low hardness and high transmissive properties, such as silicone, could be used. Application end 8 may be a lens itself in order to converge, diverge, or collimate the light energy depending on a chosen application.

A material application sub-system can be integrated into the device to allow for simultaneous application of light energy and coolants, pain relievers, anti-bacterial agents, or other fluid material including water, saline, and gaseous nitrogen, oxygen, or carbon dioxide. However, unlike state-of-the-art systems, the present system can often be used without coolants, because of the application tip location monitor, which prevents over radiation.

In most applications, the cooling fluid materials preferably should be substantially transmissive at the pre-selected operating wavelength and optimally have a refractive index substantially equivalent to the treatment material to reduce reflected light. However, in some applications, it may be advantageous for an applied fluid material to absorb some or all of the light energy. For example, for treatment applications, antibacterial agents may be activated by light energy, or, for non-medical applications, polymeric solutions may be UV-cured.

Again in FIG. 1, in a preferred embodiment, light delivery optics 3 has rectangular shaped core that may provide optimal phase space for the light energy. A rectangular core can maintain the brightness of the original light source and thus allow maximum delivery of light energy through application end 8. Additionally, by closely coupling the size and shape of the delivery fiber to that of the diode emitter, suitable power densities may be maintained without increasing the output power of the emitter. Thus, smaller delivery fibers would make for more efficient delivery of laser power at a specified density. As an alternative to a rectangular fiber core, a standard round optical fiber may be employed.

During most applications, it is difficult to visually determine which treatment areas have previously been scanned. For example, in port wine applications, the actual lightening of the lesion occurs slowly over a period of days to weeks as the body phagocytizes the necrotic tissue. A preferred embodiment of the present invention includes a sub-system that determines the position of application end 8 in relation to its starting point. This sub-system allows for greater controllability in distribution of light energy because an operator can recognize the previously treated areas and avoid applying additional radiation. To facilitate this, a three-dimensional positioning system, similar to those currently used in multimedia virtual world applications in the entertainment field, is adapted for use in medical applications. Such systems determine the position of an object without contacting its surface using supersonic acoustical waves or lasers. Such a system used in a medical application offers the advantage of allowing the physician to stop treatment and remove the hand-piece from the patient's skin, for cleaning, etc. and then replace the hand-piece. In an alternative embodiment, the patient is also connected to a three-dimensional positioning system so that the patient's movement does not affect the treatment parameters.

Figure 2:
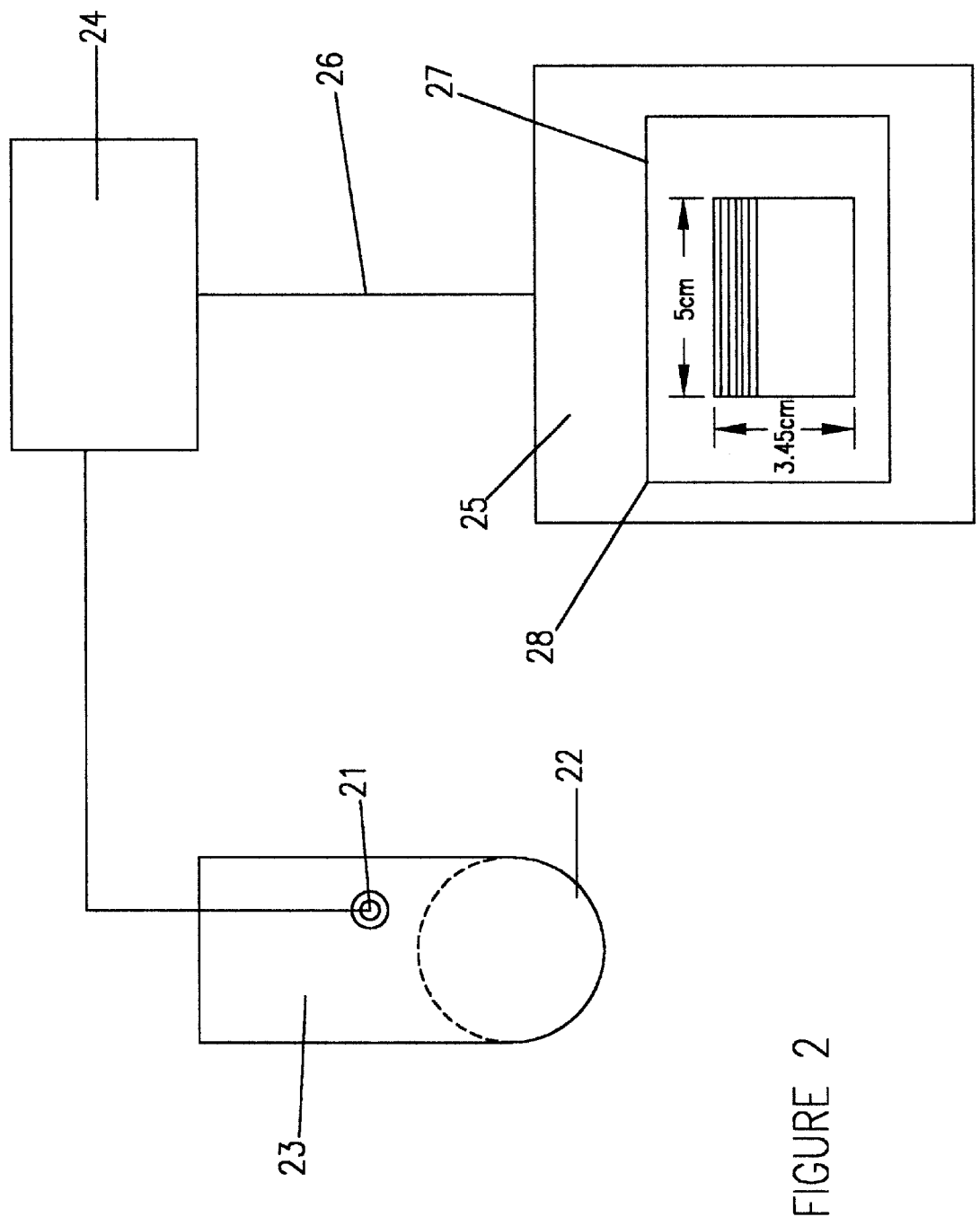
FIG. 2 shows a further embodiment of the present invention displaying visual output.

FIG. 2 illustrates an example of an embodiment where small cylinder 21 is pressed against application end 22, corresponding to 8 of FIG. 1, so that small cylinder 21 spins as application end 22 moves. The sub-system can be analogized to that of a common computer mouse. The sub-system includes opto-med encoded integrator 24 that transforms the movement of small cylinder 21 into a digital signal that can be transmitted to unit 25. Unit 25 is a monitor or computer coupled to a trigger. The sub-system is programmed to recognize the position of the device in relation to its starting point based on the distance traveled by application end 22.

In one embodiment, the dimensions of a regularly shaped work or treatment site are input into the sub-system. Once a starting point is chosen, the subsystem determines which portions of the site have been treated. If the treatment or work site is irregularly shaped, an outline of the site can be mapped by starting the hand-piece at a point along an edge of the site and scanning the entire edge until the hand-piece is in its original position. This outline provides the boundary for application of light energy, and the sub-system will determine the areas that have already received light energy treatment.

This sub-system ensures that each part of the work or treatment site will be treated only once with minimum overlap. In an embodiment of the present invention an acoustical signal is emitted by the sub-system to alert the operator if a region has been erroneously scanned. Alternatively a display unit is incorporated into the system that employs a color scheme to communicate to the operator which areas have been treated, and the quantity of light energy that has been applied to a certain portion of the site. This reduces operator error and the need for additional treatment due to under or over exposure of a site. Furthermore, since operator error is reduced by this embodiment, lower skilled people are able to operate it safely, particularly in emergency operation or for non-medical application of the invention.

In another embodiment, this sub-system is employed to regulate the delivery of light energy as a function of treatment velocity (i.e. speed and direction). For example, if a power density of 10 watts/cm$^2$ is pre-selected by the operator, the system varies the power output (i.e. frequency of pulses for a system operating non-continuously, or dosage for a system operating continuously) as the velocity of treatment is varied. Higher powers are transmitted when the hand-piece is moved quickly, and lower powers are transmitted when the hand-piece is moved more slowly. The ultimate effect is to transmit the same energy per unit area, and thus provide for a uniform fluence.

Alternatively, it may advantageous to deliver different quantities of light energy to different portions of a work or treatment site. For example, wound treatment will be more effective if a greater amount of light energy is transferred to the center of the wound and a lesser amount to the outer regions of the wound.

State-of-the-art systems that can treat large three-dimensional sites cannot provide a controllable distribution of energy. Alternatively, state-of-the-art systems that provide a uniform distribution of energy cannot treat a large three-dimensional surface. The above embodiments of the sub-system allow the present invention to be employed on a large, irregularly shaped, three-dimensional surface, while providing a uniform distribution of energy.

At the edges of the applicator, channels 11 and 12 of FIG. 1, the edges may be designed to act as scrapers to remove dead skin and other debris. This feature provides for obstruction-free treatment areas.

The photonic delivery system may be activated by back-pressure on application end 8 of FIG. 1, or by an activation switch that may be integrated onto the hand-piece. It is therefore not necessary to employ the system in contact with the work or treatment site Rather, the system may be operated in a "touchless" or non-contact mode. Additionally, for safety reasons, the delivery system may be outfitted with a dead man switch.

A touchless distance sensing system may be employed in connection with the laser applicator hand-piece to allow for radiation to be applied without contacting the work or skin surface. In an embodiment of the present invention, the laser applicator is held at a distance from the skin surface. A computerized distance sensor alerts the operating physician when the applicator is too far from the skin surface so that the physician may move the applicator into closer proximity to the skin surface. The sensor also alerts the operator when the applicator is too close to the skin surface. A second distance sensor tracks the location of the applicator in reference to its starting point and prevents the operator from repeatedly scanning the same skin surface area. Therefore, areas may be effectively scanned without contacting the skin surface. In an alternative embodiment, the patient is also connected to the sensing system to more accurately control the treated areas. Positioning system embodiments of the present invention may operate using lasers or ultrasound.

The "touchless" embodiment is particularly useful for employment in sensitive treatment areas. For example, in wound treatment direct contact could further injure the treatment site. Furthermore, in photo-activation applications where a sticky fluid substance has previously been applied at the treatment site, the use of the "touchless" hand-piece avoids complications that arise due to the adhesive properties of the fluid substance. A shaped application end (hand-piece tip) is not necessary for this embodiment, instead, an adjustable lens is employed in an alternative embodiment to focus, collimate or diffuse the light energy as required by the application.

Figure 3:
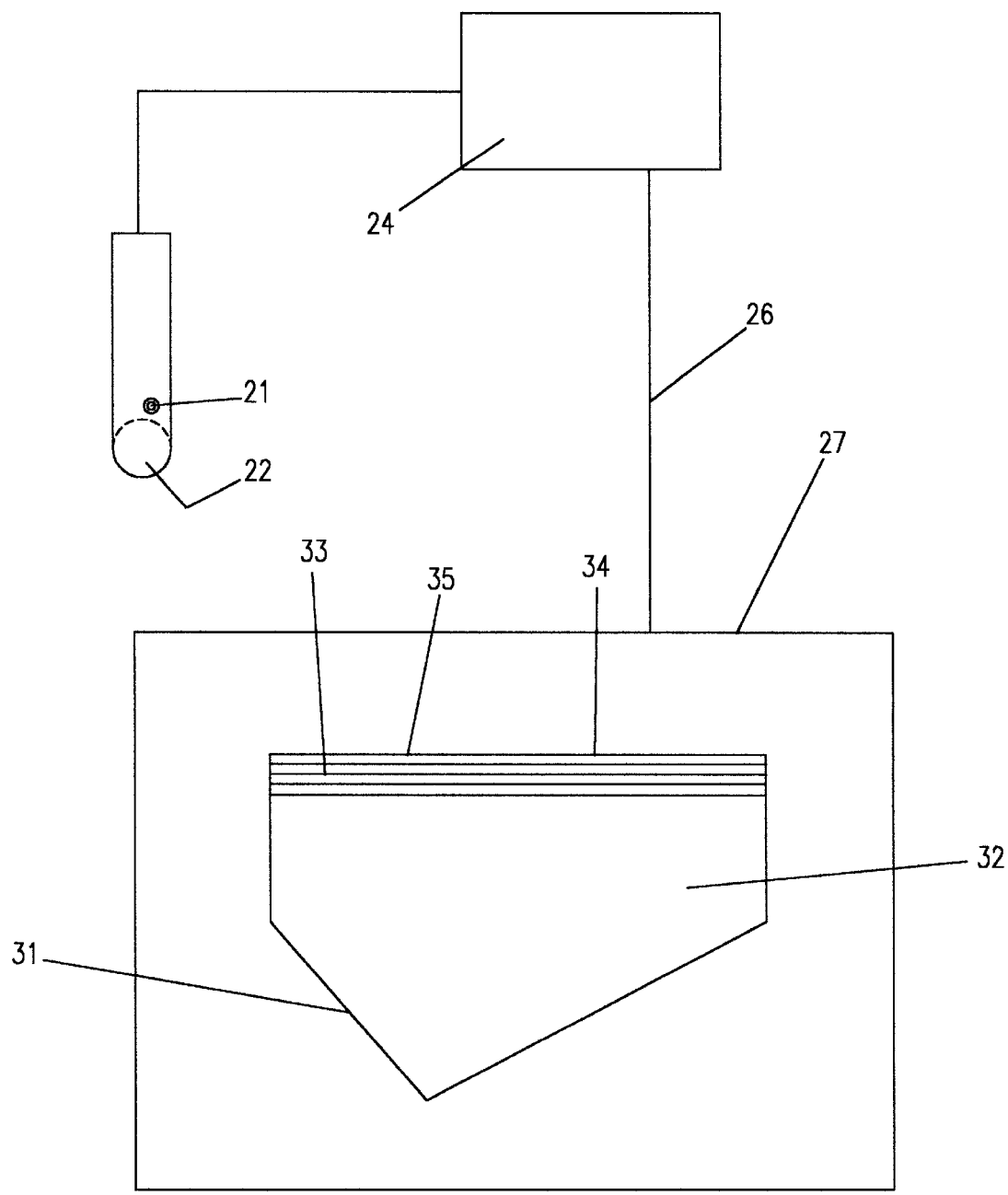
FIG. 3 depicts another preferred embodiment of the present invention displaying visual output premised on FIG. 2.

The present invention system can be used to scan irregularly shaped surfaces due to its position tracking capabilities. In FIG. 3, small cylinder 21 is pressed against application end 22, corresponding to 8 of FIG. 1, so that small cylinder 21 spins as application end 22 moves. The sub-system includes integrator 24 that transforms the movement of small cylinder 21 into a digital signal that can be transmitted to unit 25, which may be a display monitor or a computer and a trigger. The sub-system can be programmed to recognize the position of the device in relation to its starting point based on the distance traveled by application end 22. Here, unlike in FIG. 2, the treatment area is irregularly shaped.

FIG. 4a and FIG. 4b portray the outer shell of the hand-piece of the present invention. FIG. 4a is a right-handed piece and FIG. 4b is a left-handed piece. Both hand-pieces have position tracking wheels, represented by 43 in FIG. 4a and 47 in FIG. 4b.

The present invention can be used with any chosen light source depending on the application and wavelength desired. For example, in dermatological applications the light source may be a pulsed dye, carbon dioxide, erbium, ruby, argon, alexandrite, copper vapor or Nd:YAG laser. Additional light sources include, diode light sources including, but not limited to, laser diodes, tapered laser diodes, frequency-doubled laser diodes, diode pumped solid state lasers, frequency-doubled diode pumped solid state lasers, diode pumped fiber lasers, or super luminescent diodes.

The light source can be integrated with the power supply unit, or can alternatively be a separate component, which may be interchangeable with other light sources. In another alternative, the light source could be integrated into the hand-piece. For example, a diode light source could be integrated at the top of the hand-piece. In another alternative embodiment, the present device may be employed with multiple light sources having different wavelengths, thus allowing the operator greater control of the depth of photonic penetration and subsequent blood vessel coagulation. The desired light source module would be selected prior to applying the radiation to the treatment surface.

There are numerous and varied applications that this device is suitable for. For example, in hard tissue applications, hydrogen peroxide can be smeared onto teeth and then heated by light energy delivered through the hand-piece. This procedure can be employed to bleach the teeth and make them cosmetically more attractive. The soft tissue applications of the present invention include, but are not limited to: 1) the removal of vascular lesions, benign pigmented lesions and tattoos, 2) the abatement of wrinkles, scars and other blemishes, 3) the removal of unwanted hair, 3) the creation of skin pockets during hair transplantation surgery, 4) the shrinkage of varicose veins, and 5) wound treatment.

Figure 5:
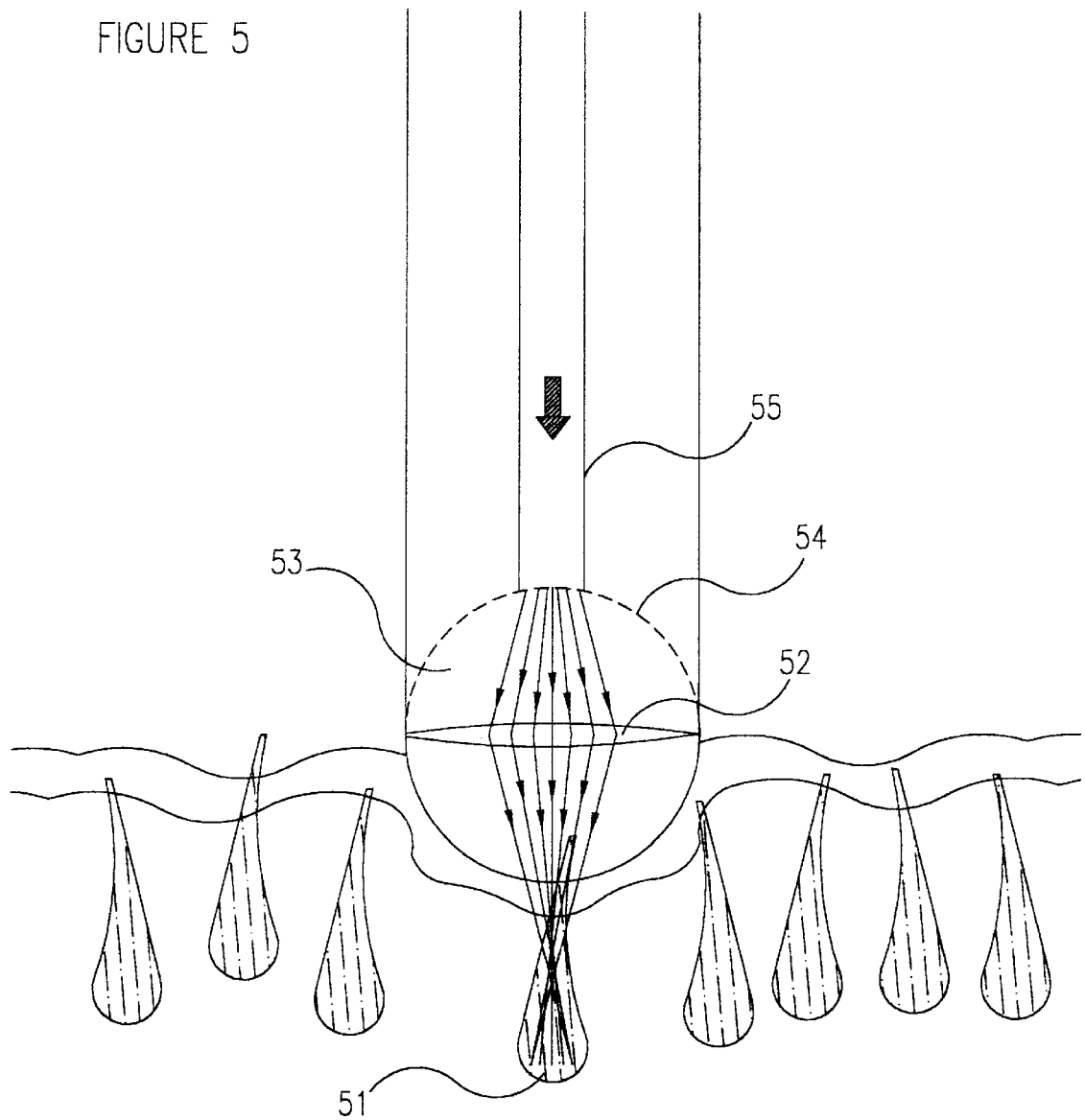
FIG. 5 exhibits a further preferred embodiment of the present invention employed for hair removal.

FIG. 5 displays another embodiment of the present invention for use in hair removal. Lens 52 can be an adjustable lens to manipulate the spot size required for certain applications. Hollow application end 54 rotates around lens 52, which continuously remains in the same orientation to light delivery optics 55, which may be a single optical fiber or bundle of optical fibers. Light energy transmitted by light delivery optics 55 propagates through application end 54 and is focused by lens 52 to hair follicle 51. The melanin within hair follicle 51 absorbs light energy causing hair follicle 51 to coagulate and be destroyed.

Figure 6:
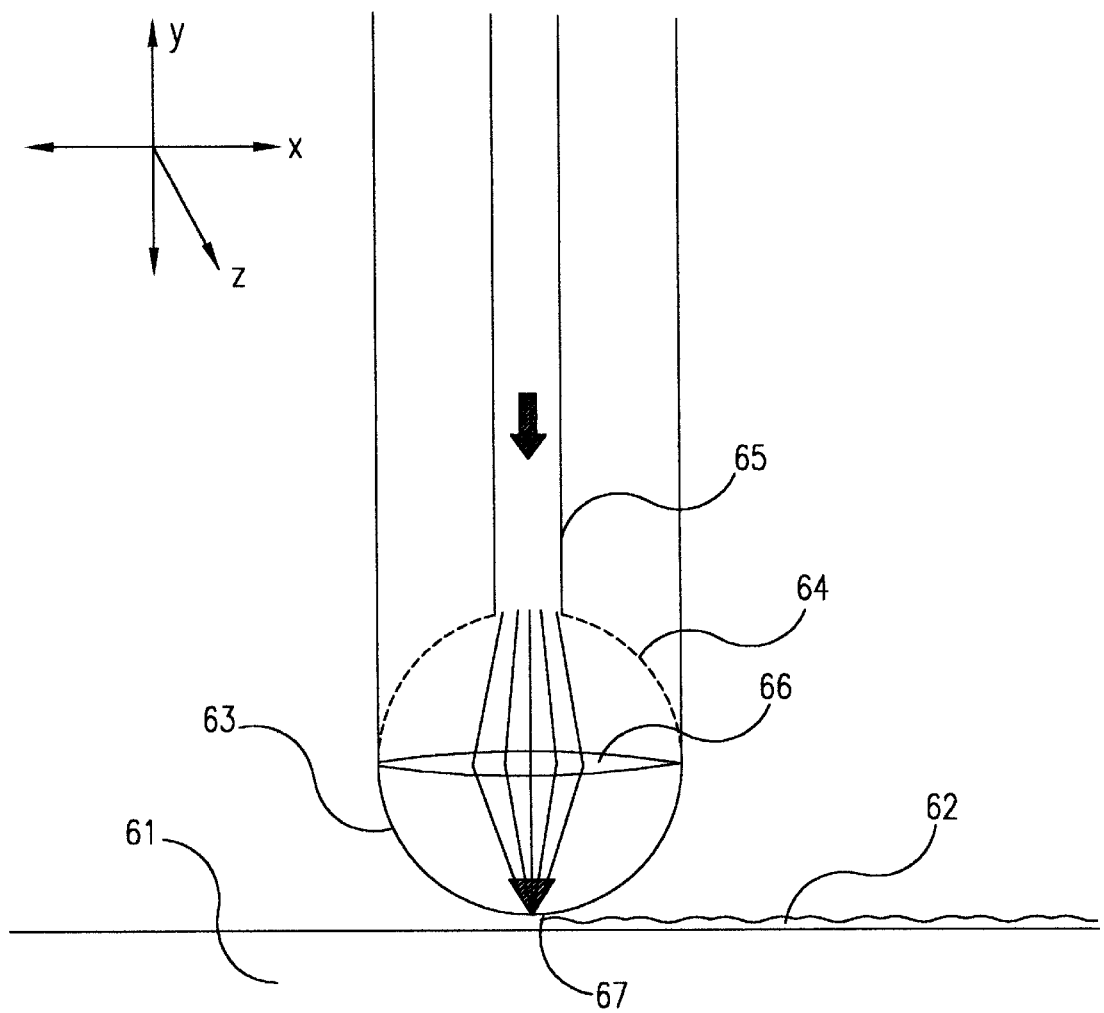
FIG. 6 presents an embodiment of the present invention employed for deposition of an adhesive film.

FIG. 6 provides an embodiment of the present invention employed for deposition of an adhesive film. In FIG. 6, 62 represents a thin adhesive film. Lens 66 can be an adjustable lens to manipulate the spot size required for certain applications, depending on the energy density needed. Applicator end 63 may be fixed with respect to light delivery optics 65, which may be a single optical fiber or bundle of optical fibers. Light energy transmitted by light delivery optics 65 propagates through application end 63 and is focused by lens 66 to film surface 67. The radiation is applied to photocurable adhesive compounds to create thin films.

The present invention may also be employed to create thin films at a substrate site. For example, thin cross-linked hydrophilic polymeric films can be produced. The present invention may be employed to smear the solution on a substrate, and irradiate the site to activate cross-linking and polymerization. These films can be suitable for application as a carrier for biologically active agents, such as pharmaceuticals, both for humans and animals, insecticides, and fertilizers; as hydrophilic membranes for separation processes; as bandages for wound treatment; as body implants or as coatings for such implants; and as coatings on glass, metal, wood or ceramics.

Having described preferred embodiments of the invention with reference to the accompanying drawings, it is to be understood that the invention is not limited to these precise embodiments, and that various changes and modifications may be effected therein by one skilled in the art without departing from the scope or spirit of the invention as defined in the appended claims.

What is claimed is:

1. A method of controllably applying radiation to an extended treatment surface comprising the steps of:

selecting a light source having a wavelength which yields a desired depth of penetration;

optically connecting said light source to a manually operated photonic scanning and delivery device;

bringing said manually operated photonic scanning and delivery device to said extended treatment surface, said surface having an area substantially larger than an optical output beam of said delivery device;

activating said light source;

manually scanning said extended treatment surface with said scanning and delivery device to apply said radiation to a selected treatment area;

employing a monitoring/measuring subsystem within said scanning and delivery device, which relays movement/position of said device to controllably deliver said radiation from said light source in a predetermined pattern; and wherein said monitoring/measuring subsystem communicates to inform an operator that a part of said extended treatment area has been treated with a quantity of a light energy from said light source to ensure that each said part of said treatment area receives a desired amount of said light energy.

2. A method of controllably applying radiation to an extended treatment surface according to claim 1, wherein said step of bringing said device to said treatment surface involves bringing said scanning and delivery device in contact with said treatment surface, and said manually scanning of said extended treatment surface is done in a contact mode.

3. A method of controllably applying radiation to an extended treatment surface according to claim 1, wherein said step of bringing said device to said treatment surface involves bringing said scanning and delivery device in proximity to said treatment surface, and said manually scanning of said extended treatment surface is done in a non-contact mode.

4. A method of controllably applying radiation to an extended treatment surface according to claim 1, wherein said step of ensuring optical connection to a selected light source involves optically connecting said device to a light source exterior to said device.

5. A method of controllably applying radiation to an extended treatment surface according to claim 1, wherein said step of optically connecting said light source to a manually operated photonic scanning and delivery device involves selecting a light source module and placing it into said scanning and delivery device.

6. A method of controllably applying radiation to an extended treatment surface according to claim 2 wherein said step of monitoring/measuring subsystem measures location by a contact mode employs a technique selected from the group consisting of a spinning cylinder/sphere, supersonic acoustical waves and lasers.

7. A method of controllably applying radiation to an extended treatment surface according to claim 3, wherein said monitoring/measuring subsystem measures location by a non-contact mode employs a technique selected from the group consisting of supersonic acoustical waves and lasers.

8. A method of controllably applying radiation to an extended treatment surface according to claim 1, wherein said monitoring/measuring subsystem communicates to an operator by an acoustical signal.

9. A method of controllably applying radiation to an extended treatment surface according to claim 1, wherein said monitoring/measuring subsystem communicates to an operator by a display unit that employs a color scheme.

* * * * *

UNITED STATES PATENT AND TRADEMARK OFFICE
CERTIFICATE OF CORRECTION

PATENT NO. : 6,406,474 B1
DATED : June 18, 2002
INVENTOR(S) : W. Neuberger and M. Quade It is certified that error appears in the above-identified patent and that said Letters Patent is hereby corrected as shown below:

<u>Title page,</u>
Item [73], Assignee, should read as follows:
-- [73] Assignee: CeramOptec Industries, Inc., East Longmeadow, MA --.

Signed and Sealed this

Eighteenth Day of March, 2003

JAMES E. ROGAN
*Director of the United States Patent and Trademark Office*